United States Patent [19]

Hines et al.

[11] Patent Number: 5,716,336
[45] Date of Patent: Feb. 10, 1998

[54] ADJUSTABLE FOOT BRACE

[76] Inventors: Kevin L. Hines, 726 First St. SW., Mason City, Iowa 50401; Paul D. Van Gerpen, 620 Golfview Dr., Garner, Iowa 50438; Ronald M. Russ, 6627 50th Ave. N., Crystal, Minn. 55428

[21] Appl. No.: 686,562
[22] Filed: Jul. 26, 1996
[51] Int. Cl.⁶ ..................................... A61F 5/00
[52] U.S. Cl. ............................. 602/27; 602/16
[58] Field of Search .................... 602/5, 16, 23, 602/27-29; 128/882

[56] References Cited

U.S. PATENT DOCUMENTS

| | | | |
|---|---|---|---|
| 1,598,504 | 8/1926 | Pierce et al. | 602/27 |
| 5,044,360 | 9/1991 | Janke | 602/27 X |
| 5,328,444 | 7/1994 | Whiteside | 602/27 X |
| 5,399,152 | 3/1995 | Habermeyer et al. | 602/27 X |
| 5,431,624 | 7/1995 | Saxton et al. | 602/27 |
| 5,453,082 | 9/1995 | Lamont | 602/27 |

*Primary Examiner*—Linda C. Dvorak

[57] ABSTRACT

An improved control for the movement of the foot in an ankle brace device. The control is adjustable to provide multiple positions of the foot simply by the pushing of a button or knob on a springing band to allow movement of the band between adjusted positions.

6 Claims, 1 Drawing Sheet

ADJUSTABLE FOOT BRACE

BACKGROUND AND SUMMARY OF THE INVENTION

This invention pertains to adjustment control devices and more particularly to a device to control the position of an ankle in an ankle brace.

In the treatment of some conditions of a leg or ankle, a brace is used to immobilize—at least for an interval—the position of the foot relative to the leg. For that purpose, it is common to use a brace molded of plastic and fitted around the calf of the leg and also having a molded position engaging the foot. Usually it is desirable to have the foot part adjustable relative to the leg position. The desirability may be different for given injuries, or may be desirable even on a given patient to allow varying positions of the foot.

By the present invention, a single brace having a hinged joint is used. The position of the foot portion of the brace relative to the leg may be adjusted to provide differing angles between the foot and the leg, and the adjustment is controlled by a novel control using a very simple and easy to use control device to hold the parts in varying adjusted positions. The relative position is readily changed by using a finger operated release on the control device.

DESCRIPTION

Figure 2:
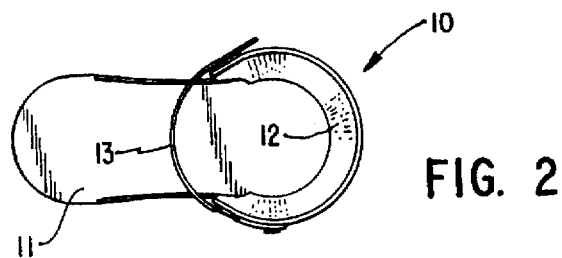
FIG. 2 is a top plan view of the brace shown in FIG. 1.
Figure 1:
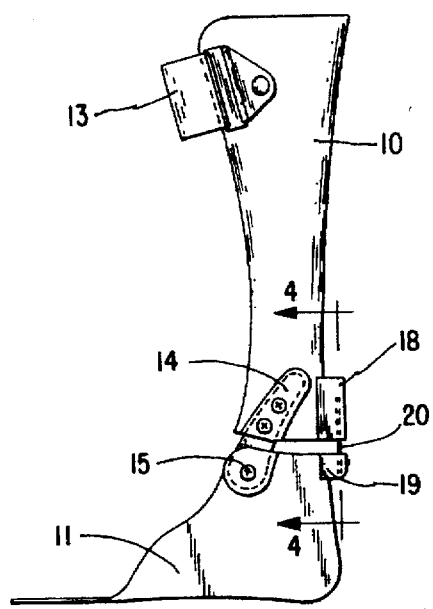
FIG. 1 is a side elevational view of a brace with the novel control in one position.
Figure 3:
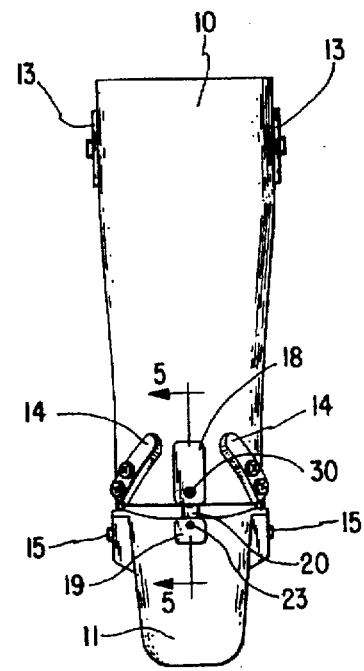
FIG. 3 is a rear elevational view of the brace of FIG. 1.

Briefly, this invention comprises an easily adjusted control for holding a patient's foot in an adjusted position relative to the leg in an adjustable ankle brace.

More specifically and referring to the drawings, the control device is proposed to be used on an ankle brace composed of a leg portion 10 and a foot support 11. The leg portion may have interior padding 12 and is held to the leg of the wearer by a strap like wrap-around 13. A hinge formed from a pair of plates 14 fastened to the leg part 10 and pivoted to the foot part 11 by axis-defining screws 15 allow adjustment of the angle between the foot part and the leg part. It is this adjustment that is to be controlled.

The control device comprises essentially an upper block 18 attached to the leg part 10 thus providing an upper support and a lower block 19 attached to the foot part 11, forming a lower support means, and may be molded into the brace. A ribbon-like control strip 20 is inserted into a chamber 22 in the lower block 19 and may be fastened there by a screw 23.

Figure 4:
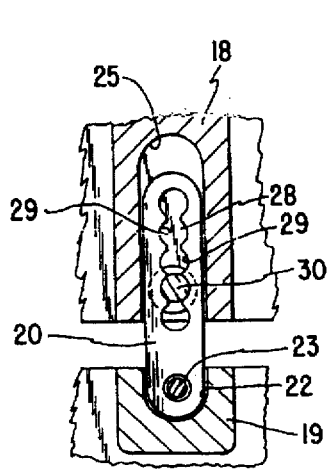
FIG. 4 is a sectional view to an enlarged scale of the control device from line 4—4 of FIG. 1.
Figure 5:
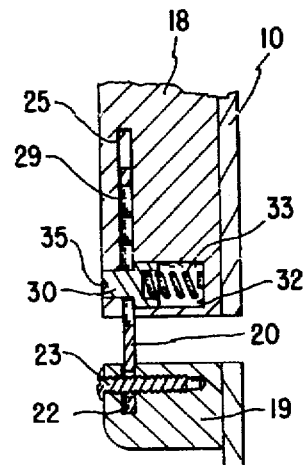
FIG. 5 is a sectional view, also to an enlarged scale, from line 5—5 of FIG. 3.
Figure 6:
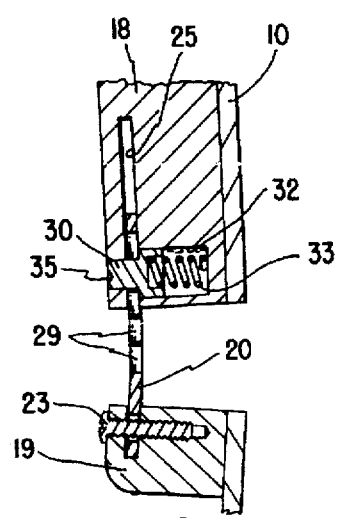
FIG. 6 is a view similar to FIG. 5 showing a different adjusted position.

The strip 20 is slidably disposed in a chamber 25 in the upper block 18 similar to the slot 22 in the lower block 19. Thus, when the foot part 11 is moved around the pivot axis 15, the strip 20 will slide within the chamber 25. That sliding movement is controlled by means best illustrated in FIGS. 4-6. As shown in FIG. 4, the strip 20 is punctured by a slot 28 formed with a series of notches 29 of arcuate form. These notches are of a size and shape to embrace the button-like tip 30 of a control plunger.

The control plunger comprises a base in the form of a piston 31 and the tip 30. The piston is slidably engaged in a cylindrical hole 32 in the upper block 18 and is urged outwardly of that hole by a compression spring 33. Thus, when the strip 20 is in place, the plunger is urged in a direction against the strip. When the notches 29 are aligned with the tip 30, that tip extends through the slot, and because of the shape of the notches, serves to stop any motion of the strip 20, and therefor of the foot part 11 relative to the leg part 10 of the brace. Disengagement of the tip 30 from the slot 28 and into notches 29 is accomplished simply by pressing the plunger back into the hole 32 against the pressure of the spring 33. To facilitate that movement, a dimple 35 may be formed in the tip 30 where the dimple may be engaged by the point of a stylus or the tip of a ball-point pen or pencil or similar object.

Thus, there is provided a conveniently adjustable ankle brace in which the angle between the leg and the foot can be adjusted easily and conveniently for any single user—even while the brace is in place or, if desired, for a user different from the original user.

I claim as my invention:

1. In combination with an ankle brace having a leg part and a foot part joined together by hinge means, control means for controlling any motion between said foot part and said leg part around said hinge means comprising first engagement means for engaging a person's leg on said leg part and second engagement means for engaging a person's foot on said foot part, an adjustment device including a sliding strip attached to one of said engagement means and slidably engaged with the other of said engagement means, said strip being formed with a slot having notched edges and stop means engageable with said notched edges to prevent motion between said one of said engagement means and said other of said engagement means.

2. The combination of claim 1 in which said stop means includes a plunger slidably disposed in a hole formed in said other of said engagement means, said plunger being engageable with said slot to hold said strip in an adjusted position.

3. The combination of claim 2 in which a spring is engaged between said plunger and said other of said engagement means whereby said plunger is biassed toward said strip.

4. The combination of claim 1 in which said stop means includes a plunger slidably moveable within a hole in said other of said engagement means, said plunger including a tip insertable into any of said notched edges whereby motion of said strip is prevented.

5. The combination of claim 4 in which a spring is engaged between said plunger and said other of said engagement means to bias said tip into said notched edges.

6. The combination of claim 5 in which said tip includes one end formed with a dimple, said dimple providing a convenient place to apply pressure counter to the biassing of said spring.

* * * * *